US010174361B2

(12) United States Patent
Skog et al.

(10) Patent No.: US 10,174,361 B2
(45) Date of Patent: Jan. 8, 2019

(54) CEREBROSPINAL FLUID ASSAY

(71) Applicant: Exosome Diagnostics, Inc., New York, NY (US)

(72) Inventors: Johan Karl Olov Skog, Charlestown, MA (US); Leileata Russo, Belmont, MA (US)

(73) Assignee: Exosome Diagnostics, Inc., Waltham, MA (US)

( * ) Notice: Subject to any disclaimer, the term of this patent is extended or adjusted under 35 U.S.C. 154(b) by 0 days.

(21) Appl. No.: 14/357,475

(22) PCT Filed: Nov. 12, 2012

(86) PCT No.: PCT/US2012/064677
§ 371 (c)(1),
(2) Date: May 9, 2014

(87) PCT Pub. No.: WO2013/071239
PCT Pub. Date: May 16, 2013

(65) Prior Publication Data
US 2015/0038335 A1 Feb. 5, 2015

Related U.S. Application Data

(60) Provisional application No. 61/558,400, filed on Nov. 10, 2011.

(51) Int. Cl.
*C12Q 1/68* (2018.01)
*C12Q 1/6806* (2018.01)
*C12Q 1/6883* (2018.01)
*C12N 15/10* (2006.01)
*C12Q 1/6886* (2018.01)

(52) U.S. Cl.
CPC ....... *C12Q 1/6806* (2013.01); *C12N 15/1003* (2013.01); *C12N 15/1017* (2013.01); *C12Q 1/6883* (2013.01); *C12Q 1/6886* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 5,219,727 | A | 6/1993 | Wang et al. |
| 5,538,871 | A | 7/1996 | Nuovo et al. |
| 5,556,773 | A | 9/1996 | Yourno |
| 5,639,606 | A | 6/1997 | Willey |
| 5,639,611 | A | 6/1997 | Wallace et al. |
| 6,004,755 | A | 12/1999 | Wang |
| 6,812,023 | B1 | 11/2004 | Lamparski et al. |
| 6,893,837 | B2 | 5/2005 | Slamon et al. |
| 6,899,863 | B1 | 5/2005 | Dhellin et al. |
| 6,913,879 | B1 | 7/2005 | Schena |
| 6,994,960 | B1 | 2/2006 | Foote et al. |
| 7,074,563 | B2 | 7/2006 | Köster |
| 7,186,512 | B2 | 3/2007 | Martienssen et al. |
| 7,198,893 | B1 | 4/2007 | Köster et al. |
| 7,198,923 | B1 | 4/2007 | Abrignani et al. |
| 7,364,848 | B2 | 4/2008 | Van Beuningen et al. |
| 7,378,245 | B2 | 5/2008 | Liu |
| 2003/0129134 | A1* | 7/2003 | Chenard et al. ............... 424/9.3 |
| 2010/0196426 | A1* | 8/2010 | Skog et al. .................... 424/400 |
| 2011/0003704 | A1 | 1/2011 | Skog et al. |
| 2011/0053157 | A1 | 3/2011 | Skog et al. |
| 2011/0177054 | A1 | 7/2011 | Gibbings et al. |
| 2011/0182814 | A1* | 7/2011 | Kelly et al. ................... 424/9.1 |

FOREIGN PATENT DOCUMENTS

| WO | WO 2003/023065 A1 | 3/2003 |
| WO | WO 2009/100029 A1 | 8/2009 |
| WO | WO 2010/083252 A2 * | 7/2010 |
| WO | WO 2011/009104 * | 1/2011 |
| WO | WO 2011/031877 A1 | 3/2011 |
| WO | WO 2011/031892 A1 | 3/2011 |
| WO | WO 2011/050129 A1 * | 4/2011 |
| WO | WO 2012/064993 A1 | 5/2012 |
| WO | WO 2013/071239 A1 | 5/2013 |

OTHER PUBLICATIONS

Huttner Hagen B. et al., "The stem cell marker prominin-1/CD 133 on membrane particles in human cerebrospinal fluid offers novel approaches for studying central nervous system disease", Stem Cells (Miamisburg), 2008, pp. 698-705, vol. 26.
Abravaya, et al., "Detection of point mutations with a modified ligase chain reaction (Gap-LCR)." Nucleic Acids Research (1995); 23(4): 675-682.
Al-Nedawi, et al., "Intercellular transfer of the oncogenic receptor EGFRvIII by microvesicles derived from tumour cells." Nat Cell Biol. (2008); 10(5): 619-624.
Balzar, et al., "The biology of the 17-1A antigen (Ep-CAM)." J Mol Med. (1999); 77(10): 699-712.
Chen, et al., "Microfluidic isolation and transcriptome analysis of serum microvesicles." Lab Chip (2010); 10(4): 505-511.
Cheruvanky, et al., "Rapid isolation of urinary exosomal biomarkers using a nanomembrane ultrafiltration concentrator." Am J Physiol Renal Physiol. (2007); 292: F1657-F1661.
Cotton, et al., "Reactivity of cytosine and thymine in single-base-pair mismatches with hydroxylamine and osmium tetroxide and its application to the study of mutations." Proc Natl Acad Sci U S A (1988); 85(12): 4397-4401.
Duijvesz, et al., "Exosomes as Biomarker Treasure Chests for Prostate Cancer." European Urology (2011); 59(5): 823-831.

(Continued)

*Primary Examiner* — James S Ketter
(74) *Attorney, Agent, or Firm* — Cooley LLP; Ivor R. Elrifi; Matthew Pavao

(57) ABSTRACT

The present invention is directed to methods of isolating particles, such as nucleic acid-containing particles or microvesicles, from a biological sample and extracting nucleic acids therefrom, wherein the biological sample is cerebrospinal fluid. The present invention further provides methods for aiding diagnosis, prognosis, monitoring and evaluation of a disease or other medical condition in a subject by detecting a biomarker associated with a disease or medical condition thereof.

20 Claims, 8 Drawing Sheets

Specification includes a Sequence Listing.

(56) References Cited

OTHER PUBLICATIONS

Extended European Search Report for European Application No. EP 12847048.1, dated Jun. 11, 2016, 5 pages.
Fischer and Lerman, "[11] Two-dimensional electrophoretic separation of restriction enzyme fragments of DNA." Methods in Enzymology (1979); 68: 183-191.
Fischer and Lerman, "Length-independent separation of DNA restriction fragments in two-dimensional gel electrophoresis." Cell (1979); 16(1): 191-200.
International Preliminary Report on Patentability for International Application No. PCT/US2012/064677, dated May 13, 2014, 9 pages.
International Search Report and Written Opinion for International Application No. PCT/US2012/064677, dated Feb. 5, 2013, 11 pages.
Kan and Dozy, "Antenatal diagnosis of sickle-cell anaemia by DNA analysis of amniotic-fluid cells." The Lancet (1978); 312(8096): 910-912.
Kan and Dozy, "Polymorphism of DNA sequence adjacent to human β-globin structural gene: relationship to sickle mutation." PNAS (1978); 75(11): 5631-5635.
Kwoh, et al., "Transcription-based amplification system and detection of amplified human immunodeficiency virus type 1 with a bead-based sandwich hybridization format." Proc Natl Acad Sci U S A (1989); 86: 1173-1177.
Landegren, et al., "A ligase-mediated gene detection technique." Science (1988); 241(4869): 1077-1080.
Li, et al., "BEAMing up for detection and quantification of rare sequence variants." Nat Methods. (2006); 3(2): 95-97.
Li, et al., "Replacing PCR with Cold-PCR enriches variant DNA sequences and redefines the sensitivity of genetic testing." Nature Medicine (2008); 14(5): 579-584.
Lipson, et al., "Quantification of the yeast transcriptome by single-molecule sequencing." Nature Biotechnology (2009); 27(7): 652-658.
Miele, et al., "Autocatalytic replication of a recombinant RNA." J Mol Biol. (1983); 171: 281-295.
Miranda, et al., "Nucleic acids within urinary exosomes/microvesicles are potential biomarkers for renal disease." Kidney International (2010); 78(2): 191-199.
Myers, et al., "Detection of single base substitutions by ribonuclease cleavage at mismatches in RNA:DNA duplexes." Science (1985); 230(4731): 1242-1246.
Nakazawa, et al., "UV and skin cancer: specific p53 gene mutation in normal skin as a biologically relevant exposure measurement." Proc Natl Acad Sci U S A. (1994); 91: 360-364.
Nilsson, et al., "Prostate cancer-derived urine exosomes: a novel approach to biomarkers for prostate cancer." British Journal of Cancer (2009); 100: 1603-1607.
Orita, et al., "Detection of polymorphisms of human DNA by gel electrophoresis as single-strand conformation polymorphisms." PNAS (1989); 86(8): 2766-2770.
Raposo, et al., "B lymphocytes secrete antigen-presenting vesicles." Journal of Experimental Medicine (1996); 183: 1161-1172.
Skog, et al., "Glioblastoma microvesicles transport RNA and proteins that promote tumour growth and provide diagnostic biomarkers." Nature Cell Biology (2008); 10(12): 1470-1476.
Steemers, et al., "Whole-genome genotyping with the single-base extension assay." Nature Methods (2006); 3: 31-33.
Taylor and Gercel-Taylor, "MicroRNA signatures of tumor-derived exosomes as diagnostic biomarkers of ovarian cancer." Gynecol Oncol. (2008); 110: 13-21.
Ting, et al., "Aberrant Overexpression of Satellite Repeats in Pancreatic and Other Epithelial Cancers." Science (2011); 331(6017): 593-596.
Velculescu, et al., "Serial Analysis of Gene Expression." Science (1995); 270(5235): 484-487.
Went, et al., "Frequent EpCam protein expression in human carcinomas." Hum Pathol. (2004); 35: 122-128.

\* cited by examiner

SEQUENCE LISTING

<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: chemically synthesized

<400> SEQUENCE: 1
ctgctggctg cgctctg					17

<210> SEQ ID NO 2
<211> LENGTH: 25
<212> TYPE: DNA
<213> ORGANISM: Artificial Sequence
<220> FEATURE:
<223> OTHER INFORMATION: chemically synthesized

<400> SEQUENCE: 2
cgtgatctgt caccacataa ttacc				25

```
<210> SEQ ID NO 3
<211> LENGTH: 18
<212> TYPE: DNA
<213> ORGANISM: Artificial Sequence
<220> FEATURE:
<223> OTHER INFORMATION: chemically synthesized

<400> SEQUENCE: 3
ttcctccaga gcccgact                                                    18
```

CEREBROSPINAL FLUID ASSAY

RELATED APPLICATIONS

This application is a national stage application, filed under 35 U.S.C. § 371, of PCT Application No. PCT/US2012/064677, filed Nov. 12, 2012, which claims the benefit of and priority to U.S. Provisional Application No. 61/558,400, filed Nov. 10, 2011, the contents of each of which are incorporated by reference in their entireties.

INCORPORATION OF SEQUENCE LISTING

The contents of the text file named "EXOS006N01US_ST25.txt", which was created on Oct. 23, 2014 and is 4 KB in size, are hereby incorporated by reference in their entirety.

FIELD OF INVENTION

The present invention relates to the general fields of nucleic acid extraction from a biological sample, particularly the isolation of nucleic acid-containing particles from body fluids such as spinal fluid and extraction of nucleic acids from the isolated particles.

BACKGROUND

In research and development, as well as commercial applications of nucleic acid biomarkers, it is desirable to extract high quality nucleic acids from biological samples in a consistent, reliable, and practical manner. An object of the present invention is therefore to provide a method for quick and easy isolation of nucleic acid-containing particles from biological samples such as body fluids, e.g., spinal fluid, and extraction of high quality nucleic acids from the isolated particles. The method of the invention may be suitable for adaptation and incorporation into a compact device or instrument for use in a laboratory or clinical setting, or in the field.

SUMMARY OF THE INVENTION

The present invention is based on the discovery of methods for isolating of nucleic acid-containing particles from spinal fluid samples, and successfully extracting nucleic acids from the isolated particles. The methods disclosed herein are particularly useful for diagnosis, prognosis, or monitoring of diseases or medical conditions that affect the brain or central nervous system.

The present invention provides a method of extracting nucleic acids from a biological sample, comprising the steps of isolating nucleic acid-containing particles from the biological sample by one or more centrifugation procedures, wherein none of the centrifugation procedures are performed at a speed exceeding about 200,000 g; performing one or more steps to mitigate adverse factors that prevent or might prevent high quality nucleic acid extraction; and extracting nucleic acids from the isolated particles.

The present invention also provides a method for aiding in the diagnosis of a disease or other medical condition in a subject, comprising the steps of obtaining a nucleic acid sample from a subject, wherein the sample was obtained from a fraction of nucleic acid-containing particles isolated from a biological sample from the subject; and detecting within the nucleic acid sample the presence or absence of one or more nucleic acid biomarkers associated with a known disease or other medical condition.

The present invention further provides a method of aiding in patient monitoring for the progression or reoccurrence of a disease or other medical condition, comprising the steps of obtaining a nucleic acid sample from a patient, wherein the sample was obtained from a fraction of nucleic acid-containing particles isolated from a biological sample from the patient; and detecting within the nucleic acid sample the presence or absence of one or more nucleic acid biomarkers associated with the progression or reoccurrence of a disease or other medical condition.

The present invention further provides a method of aiding in the evaluation of treatment efficacy for a subject undergoing or contemplating treatment for a disease or other medical condition, comprising the steps of obtaining a nucleic acid sample from a subject, wherein the sample was obtained from a fraction of nucleic acid-containing particles isolated from a biological sample from the subject; and detecting within the nucleic acid sample the presence or absence of one or more nucleic acid biomarkers associated with treatment efficacy for subjects undergoing or contemplating treatment for a disease or other medical condition.

In any of the foregoing methods, the fraction of nucleic acid-containing particles isolated from a biological sample from the subject from the first step is obtained by size exclusion chromatography, density gradient centrifugation, differential centrifugation, nanomembrane ultrafiltration, filtration concentration, immunoabsorbent capture, affinity purification, ion exchange chromatography, microfluidic separation, or combinations thereof. In any of the foregoing methods, the detecting in the second step is performed by microarray analysis, PCR, hybridization with allele-specific probes, enzymatic mutation detection, ligation chain reaction (LCR), oligonucleotide ligation assay (OLA), flow-cytometric heteroduplex analysis, chemical cleavage of mismatches, mass spectrometry, nucleic acid sequencing, single strange conformation polymorphism (SSCP), denaturing gradient gel electrophoresis (DGGE), temperature gradient gel electrophoresis (TGGE), restriction fragment polymorphisms, serial analysis of gene expression (SAGE) or combinations thereof.

The present invention further provides a method for diagnosis, prognosis, monitoring or therapy selection for a disease or medical condition of a subject, comprising the steps of: obtaining a CSF sample from a subject; processing the CSF sample to remove cells and cell debris while retaining a nucleic acid-containing particle fraction from the CSF sample; extracting one or more nucleic acids from the nucleic acid-containing particle fraction; detecting a level of expression for a biomarker associated with a disease or medical condition in the extracted nucleic acids, and detecting a level of expression of a reference gene; and determining a normalized, relative expression level of the biomarker, wherein the relative expression level of the biomarker is a ratio between the level of biomarker expression to the level of reference gene expression, wherein the subject is identified as suffering from, or being at an increased risk for, the disease or medical condition when the relative expression level of the biomarker is greater than or less than a cutoff level of biomarker expression. In some embodiments, the cutoff level of biomarker expression is a score based on a collective level of biomarker expression in a control group of subjects that are not suffering from the medical condition of the prostate. In another embodiment, the cutoff level of biomarker expression is a score based on a collective level of biomarker expression in a control group of subjects that have been diagnosed with a low level or early stage of the disease or medical condition. The reference gene is a brain-associated gene, for example, U6.

In any of the foregoing methods, the biological sample is a spinal fluid sample. Preferably, the spinal fluid sample is a cerebrospinal fluid sample. In any of the foregoing methods, the biomarker is a species of nucleic acid; the level of expression of a nucleic acid; a nucleic acid variant; or a combination thereof. In some embodiments, the biomarker is messenger RNA, microRNA, siRNA or shRNA. In another embodiment, the biomarker is a nucleic acid and the method further comprises amplification of the nucleic acid. Preferably, the biomarker is associated with the brain. In some embodiments, the biomarker is associated with glioblastoma or other brain cancer, such as an EGFR variant or EGFRvIII. In some embodiments, the biomarker is associated with Alzheimer's disease or other neurodegenerative disease. For example, the biomarker is APP, Aβ42, BACE-1, Tau or a combination thereof.

The subject or patient is a human subject or patient. In some embodiments, the subject or patient is a pediatric subject or patient.

The disease or other medical condition is a brain cancer or a neurodegenerative disease. For example, the brain cancer is glioblastoma. For example, the neurodegenerative disease is Alzheimer's disease.

The present invention also provides a kit for use in any of the foregoing methods, comprising the following components: RNase inhibitor; RNA purification reagent; optionally, lysis buffer; and optionally, instructions for using the foregoing reagents in the extraction of nucleic acids from isolated particles.

DETAILED DESCRIPTION OF THE INVENTION

Figure 1A:
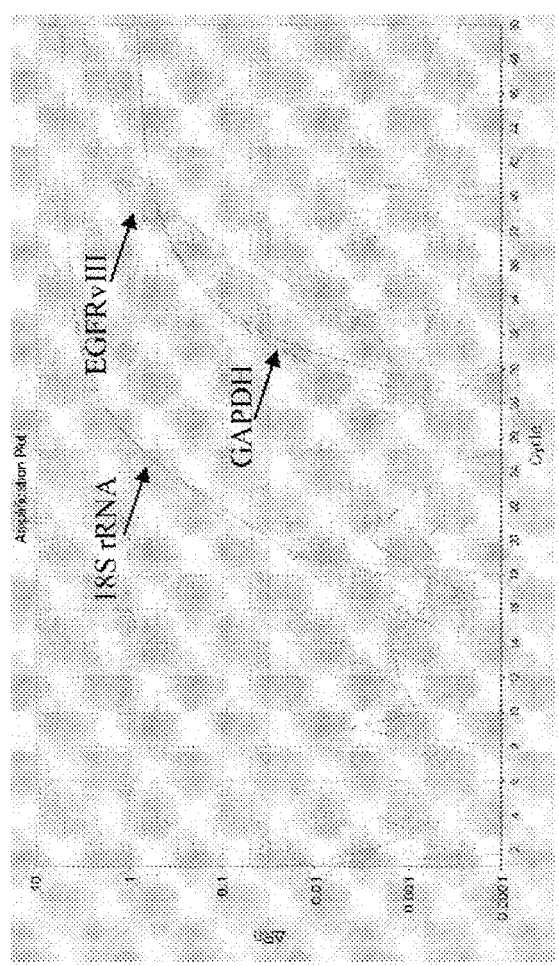
FIGS. 1A and 1B are plots of EGFRvIII amplification curves in RT-PCT analysis of RNA extracted from matched brain biopsy tissue (FIG. 1A) and cerebrospinal fluid (FIG. 1B) samples from a glioblastoma patient (Patient #1). The x-axis represents the number of PCR amplification cycles. The y-axis represents the ΔRn, which is the magnitude of the signal generated by the given set of PCR conditions.

Cell-derived vesicles are heterogeneous in size with diameters ranging from about 10 nm to about 5000 nm. For example, "exosomes" have diameters of approximately 30 to 100 nm, with shedding particles and apoptotic bodies often described as larger (Orozco and Lewis, 2010). Exosomes, shedding particles, microparticles, nanovesicles, apoptotic bodies, nanoparticles and membrane vesicles co-isolate using various techniques and will, therefore, collectively be referred to throughout this specification as "particles" unless otherwise expressly denoted.

Other nucleic acid-containing particles, e.g., RNA-protein complexes and DNA-protein complexes, may co-isolate with particles using the various methods and techniques described herein. Accordingly, the generic term "particles" will be used herein to refer to particles, RNA-protein complexes, DNA-protein complexes, circulating cells, and any other nucleic acid-containing particles that could be isolated according to the methods and techniques described herein. The methods and techniques described herein are equally applicable to the isolation of RNA-protein complexes, DNA-protein complexes, or other nucleic acid-containing particles, and particles of all sizes (either as a whole, as select subsets, or as individual species).

The present invention is partially directed to novel methods for isolating particles from a biological sample and extracting nucleic acids from the isolated particles. The nucleic acid extractions obtained by the methods described herein may be useful for various applications in which high quality nucleic acid extractions are required or preferred.

In the foregoing methods, the biological sample is preferably a spinal fluid sample. Preferably, the spinal fluid sample is a cerebrospinal fluid (CSF) sample. Cerebrospinal fluid (CSF) is a clear colorless bodily fluid produced in the choroid plexus of the brain. The primary function of the CSF is to cushion the brain within the skull and serve as a shock absorber for the central nervous system. CSF also circulates nutrients and chemicals filtered from the blood and removes waste products from the brain. It acts as a cushion or buffer for the cortex, providing a basic mechanical and immunological protection to the brain inside the skull and serves a vital function in cerebral autoregulation of cerebral blood flow. Examining the fluid can be useful in diagnosing many diseases of the nervous system.

A cerebrospinal fluid sample from a subject may be obtained in many different ways. In some instances, a CSF sample may be collected and subjected to the procedure in the method almost immediately. In other instances, a CSF sample is collected and stored in an appropriate condition for future analysis. The storage condition may be in a 4° C. environment or similar environment, or in a less than −70° C. or similar environment for long-term storage, such that the storage conditions do not significantly affect the quality of future particle isolation, particle fraction procurement, or nucleic acid extraction and biomarker analysis. A CSF sample can be obtained by methods known in the art, for example, lumbar puncture or spinal tap. CSF samples can be collected by a skilled clinical practitioner. A series of sample collections may be carried out in a certain time interval, e.g., every 6 hours, or in a scenario interval, e.g., before and after a therapeutic intervention.

The term "subject" is intended to include all animals shown to or expected to have nucleic acid-containing particles and/or circulating nucleic acids in CSF. In particular embodiments, the subject is a mammal; for example, a human or nonhuman primate, a dog, a cat, a horse, a cow or another farm animal, or a rodent (e.g. a mouse, rat, guinea pig. etc.).

The quantity of the CSF sample may vary depending on how much nucleic acid is needed for each analysis, how many times the analysis needs to be carried out, or how many different biomarkers need to be analyzed. The amount may be 1 ml, 5 ml, 10 ml, 20 ml, or 50 ml, or any amount that is deemed necessary to obtain a desired analytical result. Generally, a sample of 4 ml is used for particle isolation and nucleic acid extraction.

Isolation of Particles

The isolation of nucleic acid-containing particles, such as microvesicles or exosomes, from a biological sample prior to extraction of nucleic acids is advantageous for the following reasons: 1) extracting nucleic acids from such particles provides the opportunity to selectively analyze disease-specific nucleic acids obtained by isolating disease-specific particles apart from other particles within the fluid sample; 2) nucleic acid-containing particles produce significantly higher yields of nucleic acid species with higher integrity as compared to the yield/integrity obtained by extracting nucleic acids directly from the fluid sample without first isolating particles; 3) scalability, e.g., to detect nucleic acids expressed at low levels, the sensitivity can be increased by concentrating particles from a larger volume of sample using the methods described herein; 4) more pure or higher quality/integrity of extracted nucleic acids in that proteins, lipids, cell debris, cells and other potential contaminants and PCR inhibitors that are naturally found within biological samples are excluded before the nucleic acid extraction step; and 5) more choices in nucleic acid extraction methods can be utilized as isolated particle fractions can be of a smaller volume than that of the starting sample volume, making it possible to extract nucleic acids from these fractions or pellets using small volume column filters.

Such nucleic acid-containing particles may also contain proteins of interest, i.e., biomarkers of disease or other medical conditions. Procuring such particles from a biological sample for the purpose of protein extraction and subsequent analysis would have similar benefits to that of the nucleic acid extractions discussed above.

Methods for procuring particles from a biological sample are described in this application as well as in scientific publications and patent applications (Chen et al., 2010; Miranda et al., 2010; Skog et al., 2008). See also WO 2009/100029, WO 2011/009104, WO 2011/031892, and WO 2011/031877. These publications are incorporated herein by reference for their disclosures pertaining to microvesicle isolation or fraction procurement methods and techniques. These methods can include steps to evaluate the RNA integrity of an isolated microvesicle fraction, for example, by detecting the level of 18S and 28S RNA expression within the fraction, and also steps to evaluate protein content.

For example, a method of differential centrifugation is described in a paper by Raposo et al. (Raposo et al., 1996), a paper by Skog et al. (Skog et al., 2008) and a paper by Nilsson et al. (Nilsson et al., 2009). Methods of ion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel Taylor (Taylor and Gercel-Taylor, 2008). A method of nanomembrane ultrafiltration concentration is described in a paper by Cheruvanky et al. (Cheruvanky et al., 2007). A method of Percoll gradient isolation is described in a publication by Miranda et al (Miranda et al., 2010). Further, particles may be identified and isolated from bodily fluid of a subject by a microfluidic device (Chen et al., 2010). In research and development, as well as commercial applications of nucleic acid biomarkers, it is desirable to extract high quality nucleic acids from biological samples in a consistent, reliable, and practical manner. An object of the present invention is therefore to provide a method for quick and easy isolation of nucleic acid-containing particles from biological samples such as body fluids and extraction of high quality nucleic acids from the isolated particles. The method of the invention may be suitable for adaptation and incorporation into a compact device or instrument for use in a laboratory or clinical setting, or in the field.

The present invention provides a method for isolating, purifying, or enriching for particles from a cerebrospinal fluid sample. In some embodiments, the method comprises one or more of any of the following steps or a combination thereof: centrifugation (e.g., differential centrifugation), filtration (e.g., ultrafiltration or nanofiltration), concentration, gel permeation chromatography, ion-exchange chromatography, size-exclusion chromatography, and affinity chromatography steps, or some combination thereof.

In some embodiments, a pre-processing step prior to isolation, purification or enrichment of the particles is performed to remove large unwanted particles, cells and/or cell debris and other contaminants present in the biological sample. The pre-processing steps may be achieved through one or more centrifugation steps (e.g., differential centrifugation) or one or more filtration steps (e.g., ultrafiltration), or a combination thereof. Where more than one centrifugation pre-processing steps are performed, the biological sample may be centrifuged first at the lower speed and then at the higher speed. If desired, further suitable centrifugation pre-processing steps may be carried out. For example, the sample is centrifuged at 20,000 g for 1 hour at 4° C. To remove large unwanted particles, cells, and/or cell debris, the samples may be centrifuged at a low speed of about 100-500 g, preferably about 250-300 g. Alternatively or in addition, the samples may be centrifuged at a higher speed. Suitable centrifugation speeds are up to about 200,000 g; for example from about 2,000 g to less than about 200,000 g. Speeds of above about 15,000 g and less than about 200,000 g or above about 15,000 g and less than about 100,000 g or above about 15,000 g and less than about 50,000 g are preferred. Speeds of from about 18,000 g to about 40,000 g or about 30,000 g; and from about 18,000 g to about 25,000 g are more preferred. Particularly preferred is a centrifugation speed of about 20,000 g. Generally, suitable times for centrifugation are from about 5 minutes to about 2 hours, for example, from about 10 minutes to about 1.5 hours, or more preferably from about 15 minutes to about 1 hour. A time of about 0.5 hours may be preferred. It is sometimes preferred to subject the biological sample to centrifugation at about 20,000 g for about 0.5 hours. However the above speeds and times can suitably be used in any combination (e.g., from about 18,000 g to about 25,000 g, or from about 30,000 g to about 40,000 g for about 10 minutes to about 1.5 hours, or for about 15 minutes to about 1 hour, or for about 0.5 hours, and so on). The centrifugation step or steps may be carried out at below-ambient temperatures, for example at about 0-10° C., preferably about 1-5° C., e.g., about 3° C. or about 4° C.

Alternatively or in addition to the one or more centrifugation pre-processing steps, the biological sample may be filtered. A filter having a size in the range about 0.1 to about 1.0 μm may be employed, preferably about 0.8 μm or 0.22 μm. The filtration may also be performed with successive filtrations using filters with decreasing porosity. For example, a biological sample may be first centrifuged at 20,000 g for 1 hour to remove large unwanted particles; the sample can then be filtered, for example, through a 0.8 μm filter. In some embodiments, the filtration may have a 100 kDa cutoff value.

In some embodiments, one or more concentration steps are performed, in order to reduce the volumes of sample to be treated during the chromatography stages. Concentration may be through centrifugation of the sample at high speeds, e.g. between 10,000 and 100,000 g, to cause the sedimentation of the particles. This may consist of a series of differential centrifugations. The particles in the pellet obtained may be reconstituted with a smaller volume and in a suitable buffer for the subsequent steps of the process. The concentration step may also be performed by ultrafiltration. In fact, this ultrafiltration both concentrates the biological sample and performs an additional purification of the particle fraction. In another embodiment, the filtration is an ultrafiltration, preferably a tangential ultrafiltration. Tangential ultrafiltration consists of concentrating and fractionating a solution between two compartments (filtrate and retentate), separated by membranes of determined cut-off thresholds. The separation is carried out by applying a flow in the retentate compartment and a transmembrane pressure between this compartment and the filtrate compartment. Different systems may be used to perform the ultrafiltration, such as spiral membranes (Millipore, Amicon), flat membranes or hollow fibres (Amicon, Millipore, Sartorius, Pall, GF, Sepracor). Within the scope of the invention, the use of membranes with a cut-off threshold below 1000 kDa, preferably between 100 kDa and 1000 kDa, or even more preferably between 100 kDa and 600 kDa, is advantageous.

In some embodiments, one or more ion-exchange chromatography steps are performed. Ion exchange chromatography separates compounds based on net surface charge. Molecules are classified as either anions (having a negative charge) or cations (having a positive charge). Some molecules (e.g., proteins and microvesicles) may have both an anionic and cationic group, but may have an overall net negative or positive surface charge. A positively-charged support (anion exchanger) will bind a compound with an overall negative charge. Conversely, a negatively-charged support (cation exchanger) will bind a compound with an overall positive charge. Preferably, a positively-charged support is used in the methods described herein to isolate, purify, or enrich particles from a CSF sample.

In some embodiments, one or more size-exclusion chromatography step or gel permeation chromatography steps are performed. To perform the gel permeation chromatography step, a support selected from silica, acrylamide, agarose, dextran, ethylene glycol-methacrylate co-polymer or mixtures thereof, e.g., agarose-dextran mixtures, are preferably used. For example, such supports include, but are not limited to: SUPERDEX® 200HR (Pharmacia), TSK G6000 (TosoHaas) or SEPHACRYL® S (Pharmacia).

In some embodiments, one or more affinity chromatography steps are performed. Some particles can also be characterized by certain surface molecules. Because particles form from budding of the cell plasma membrane, these particles often share many of the same surface molecules found on the cells they originated from. As used herein, "surface molecules" refers collectively to antigens, proteins, lipids, carbohydrates, and markers found on the surface or in or on the membrane of the particle. These surface molecules can include, for example, receptors, tumor-associated antigens, membrane protein modifications (e.g., glycosylated structures). For example, particles that bud from tumor cells often display tumor-associated antigens on their cell surface. As such, affinity chromatography or affinity exclusion chromatography can also be utilized in combination with the methods provided herein to isolate, identify, and or enrich for specific populations of particles from a specific donor cell type (Al-Nedawi et al., 2008; Taylor and Gercel-Taylor, 2008). For example, tumor (malignant or non-malignant) microvesicles carry tumor-associated surface antigens and may be detected, isolated and/or enriched via these specific tumor-associated surface antigens. In one example, the surface antigen is epithelial cell adhesion molecule (Ep-CAM), which is specific to particles from carcinomas of long, colorectal, breast, protate, head and neck, and hepatic origin, but not of hematological cell origin (Balzar et al., 1999; Went et al., 2004). Additionally, tumor-specific particles can also be characterized by the lack of certain surface markers, such as CD80 and CD86. In these cases, particles with these markers may be excluded for further analysis of tumor specific markers, e.g., by affinity exclusion chromatography. Affinity chromatography can be accomplished, for example, by using different supports, resins, beads, antibodies, aptamers, aptamer analogs, molecularly imprinted polymers, or other molecules known in the art that specifically target desired surface molecules on particles.

Nucleic Acid Extraction

Methods for nucleic acid extraction are generally based on procedures well-known in the art. Persons of skill will select a particular extraction procedure as appropriate for the particular biological sample. Examples of extraction procedures are provided in patent publications WO/2009/100029, US 2010/0196426, US 2011/0003704, US 2011/0053157, WO 2011/009104, and WO 2011/031892. These publications are incorporated herein by reference for their disclosure pertaining to microvesicle nucleic acid extraction methods and techniques.

As used herein, the term "nucleic acids" refer to DNA and RNA. The nucleic acids can be single stranded or double stranded. In some instances, the nucleic acid is DNA. In some instances, the nucleic acid is RNA. RNA includes, but is not limited to, messenger RNA, transfer RNA, ribosomal RNA, non-coding RNAs, microRNAs, and HERV elements.

In some embodiments, the methods disclosed herein comprise one or more steps to mitigate adverse factors that prevent or might prevent high quality nucleic acid extraction. Such steps include the addition of RNase inhibitor or washing of the sample. In the methods described herein, an RNase inhibitor is added to the sample after microvesicle isolation and purification, but prior to microvesicle lysis and nucleic acid extraction for the purpose of preventing undesirable degradation of the nucleic acids after extraction. The microvesicles are lysed in the present of RNase inhibitor. The lysate is then added to an RNA-binding column, under such conditions known in the art so that the microvesicle RNA binds to the column. Optionally, the column is washed to increase the quality and yield of the RNA. Then the RNA is eluted under conditions known in the art such that high quality RNA is collected.

Control particles can be added during particle isolation from the CSF sample or nucleic acid extraction process for the purpose of determining the quality of the particle isolation or nucleic acid extraction. For example, the control particle contains a control nucleic acid which is detected sequence to be detected or measured for the quantification of the amount of control particle in a sample. In one aspect, the control particle is Q-beta bacteriophage and the control target gene is the Q-beta coat protein gene. In some aspects of the present invention, the control target gene is measured by amplification techniques, using specific primers that recognize the control target gene. In some aspects, a probe is utilized to detect the amplified control target gene. In some aspects, the control target gene is measured by RT-PCR analysis.

In some embodiments, proteins may also be extracted from the particles isolated from the biological sample, or CSF. Proteins can be extracted from the particles by any method known in the art, such as freeze-thaw cycles, sonication, filtration and permeabilization by organic solvents. Specific proteins of interest can be isolated and analyzed by filtration, liquid chromatography and affinity purification.

Detection of Nucleic Acid Biomarkers

Biomarker detection can be carried out on the extracted nucleic acids in many different ways and constitute many aspects. In some embodiments, the detection of nucleic acid biomarkers from one or more urine samples is to obtain a profile of all or portions of the extracted nucleic acids.

A profile, as the term is used herein, refers to a representation of particular features of a collection of nucleic acids, which can be determined through the quantitative or qualitative analysis of one or more nucleic acids contained in particles isolated from a urine sample from a subject. A reference profile is here defined as a profile obtained from an independent subject or a group of subject, or from the same subject at a different time point.

The nucleic acids in particles can be one or more types of nucleic acids, examples of which are provided herein.

The nucleic acids can be RNA. RNA can be coding RNA, e.g., messenger RNA which may encode proteins. RNA can also be non-coding RNA (ncRNA), e.g., ribosomal RNA, transfer RNA, microRNA, and other non-coding transcripts that may originate from genomic DNA. These non-coding RNA transcripts may include transcripts that are transcribed from satellite repeats; and transposons which may be DNA transposons or retrotransposons.

The nucleic acids can be DNA. DNA can be single-stranded DNA, that is reverse transcribed from RNA, e.g., cDNA. Reverse transcription is usually mediated by reverse transcriptase encoded by a reverse transcriptase gene in a cell. The DNA can also be single stranded DNA that is generated during DNA replication. Genomic DNA replicates in the nucleus while the cell is dividing. Some of the replicated DNA may come off its template, be exported out of the nucleus, and packaged in particles. The DNA can further be fragments of double-stranded DNA.

In addition, the DNA can be non-coding DNA (ncDNA). The human genome only contains about 20,000 protein coding genes, representing less than 2% of the genome. The ratio of non-coding to protein-coding DNA sequences increases as a function of developmental complexity (Mattick, 2004). Prokaryotes have less than 25% ncDNA, simple eukaryotes have between 25-50%, more complex multicellular organisms like plants and animals have more than 50% ncDNA, with humans having about 98.5% ncDNA (Mattick, 2004)

Some of the ncDNA from the genome are transcribed into ncRNAs. NcRNAs have been implicated in many important processes in the cell, e.g., enzymes (ribozymes), binding specifically to proteins (aptamers), and regulating gene activity at both the transcriptional and post-transcriptional levels.

A profile of nucleic acids can be obtained through analyzing nucleic acids obtained from isolated particles according to standard protocols in the art. For example, the analysis of the DNA may be performed by one or more various methods known in the art, including microarray analysis for determining the nucleic acid species in the extract, quantitative PCR for measuring the expression levels of genes, DNA sequencing for detecting mutations in genes, and bisulfite methylation assays for detecting methylation pattern of genes.

To obtain profiles, in some instances, data analysis may be performed. Such data analysis can be performed, for example, by Clustering Analysis, Principle Component Analysis, Linear Discriminant Analysis, Receiver Operating Characteristic Curve Analysis, Binary Analysis, Cox Proportional Hazards Analysis, Support Vector Machines and Recursive Feature Elimination (SVM-RFE), Classification to Nearest Centroid, Evidence-based Analysis, or a combination of any of the foregoing analytical techniques.

For another example, the analysis of RNA may carried out using the Digital Gene Expression (DGE) analysis method (Lipson et al., 2009). For yet another example of RNA analysis, the RNA may be digested and converted into single stranded cDNA which may then be subject to sequencing analysis on a DNA sequencing machine, e.g., the HeliScope™ Single Molecule Sequencer from Helicos BioSciences as described in a publication by Ting et al. (Ting et al., 2011).

In other instances, the RNA may be reverse-transcribed into complementary DNA (cDNA) before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. Another example of the method comprises two separate steps: a first step of reverse transcription to convert RNA into cDNA and a second step of quantifying the amount of cDNA using quantitative PCR.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., 1990), transcriptional amplification system and its variants (Kwoh et al., 1989), Qb Replicase and its variants (Miele et al., 1983), cold-PCR (Li et al., 2008), BEAMing (Li et al., 2006) or any other nucleic acid amplification methods, followed by the detection of the amplified molecules using techniques well known to those of skill in the art. Especially useful are those detection schemes designed for the detection of nucleic acid molecules if such molecules are present in very low numbers. The foregoing references are incorporated herein for their teachings of these methods. In another embodiment, the step of nucleic acid amplification is not performed. Instead, the extracted nucleic acids are analyzed directly, e.g., through next-generation sequencing.

The analysis of nucleic acids present in the isolated particles can be quantitative and/or qualitative. For quantitative analysis, the amounts (expression levels), either relative or absolute, of specific nucleic acids of interest within the isolated particles are measured with methods known in the art (described above). For qualitative analysis, the species of nucleic acids of interest within the isolated particles, whether wild type or variants, are identified with methods known in the art.

In other embodiments, the detection of nucleic acid biomarkers involves detection of the presence or absence of one or a collection of genetic aberrations. The term "genetic aberration" is used herein to refer to the nucleic acid amounts as well as nucleic acid variants within the nucleic acid-containing particles. Specifically, genetic aberrations include, without limitation, over-expression of a gene (e.g., an oncogene) or a panel of genes, under-expression of a gene (e.g., a tumor suppressor gene such as p53 or RB) or a panel of genes, alternative production of splice variants of a gene or a panel of genes, gene copy number variants (CNV) (e.g., DNA double minutes) (Hahn, 1993), nucleic acid modifications (e.g., methylation, acetylation and phosphorylations), single nucleotide polymorphisms (SNPs) (e.g., polymorphisms in Alu elements), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splice variants and/or changes of gene expression level, or combinations of any of the foregoing.

Genetic aberrations can be found in many types of nucleic acids. The determination of such genetic aberrations can be performed by a variety of techniques known to the skilled practitioner. For example, expression levels of nucleic acids, alternative splicing variants, chromosome rearrangement and gene copy numbers can be determined by microarray analysis (see, e.g., U.S. Pat. Nos. 6,913,879, 7,364,848, 7,378,245, 6,893,837 and 6,004,755) and quantitative PCR. Copy number changes may be detected, for example, with the Illumina Infinium II whole genome genotyping assay or Agilent Human Genome CGH Microarray (Steemers et al., 2006).

Nucleic acid modifications can be assayed by methods described in, e.g., U.S. Pat. No. 7,186,512 and patent publication WO/2003/023065. Methylation profiles may be determined, for example, by Illumina DNA Methylation OMA003 Cancer Panel.

SNPs and mutations can be detected by hybridization with allele-specific probes, enzymatic mutation detection, chemical cleavage of mismatched heteroduplex (Cotton et al., 1988), ribonuclease cleavage of mismatched bases (Myers et al., 1985), mass spectrometry (U.S. Pat. Nos. 6,994,960, 7,074,563, and 7,198,893), nucleic acid sequencing, single strand conformation polymorphism (SSCP) (Orita et al., 1989), denaturing gradient gel electrophoresis (DGGE) (Fischer and Lerman, 1979a; Fischer and Lerman, 1979b), temperature gradient gel electrophoresis (TGGE) (Fischer and Lerman, 1979a; Fischer and Lerman, 1979b), restriction fragment length polymorphisms (RFLP) (Kan and Dozy, 1978a; Kan and Dozy, 1978b), oligonucleotide ligation assay (OLA), allele-specific PCR (ASPCR) (U.S. Pat. No. 5,639,611), ligation chain reaction (LCR) and its variants (Abravaya et al., 1995; Landegren et al., 1988; Nakazawa et al., 1994), flow-cytometric heteroduplex analysis (WO/2006/113590) and combinations/modifications thereof.

In one embodiment, the detection of mutations is carried out by using a restriction enzyme which only digests one variant of the biomarker but not other variants of the biomarker. As is known in the art, restriction enzymes faithfully recognize particular stretches of polynucleotides and the change of one or more nucleotides within the stretch of polynucleotides will mostly likely make the polynucleotide unrecognizable and indigestible by the enzyme. As such, the detection of one variant of a biomarker may be aided by digesting away some or all of the other variants that can be recognized by the enzyme. The variant to be detected can be a wild-type variant or a mutant variant.

Gene expression levels may be determined by the serial analysis of gene expression (SAGE) technique (Velculescu et al., 1995), quantitative PCR, quantitative reverse transcription PCR, microarray analysis, and next generation DNA sequencing, as known in the art.

In general, the methods for analyzing genetic aberrations are reported in numerous publications, not limited to those cited herein, and are available to skilled practitioners. The appropriate method of analysis will depend upon the specific goals of the analysis, the condition/history of the patient, and the specific cancer(s), diseases or other medical conditions to be detected, monitored or treated.

Biomarkers Associated with Diseases or Other Medical Conditions

Many biomarkers may be associated with the presence or absence of a disease or other medical condition in a subject. Therefore, detection of the presence or absence of such biomarkers in a nucleic acid extraction from isolated particles, according to the methods disclosed herein, may aid diagnosis, prognosis, or monitoring the progress or reoccurrence of the disease or other medical condition in the subject.

For example, EGFR (epidermal growth factor receptor) was the first cell surface glycoprotein identified to be amplified and rearranged in glioblastoma multiforme (GBM) and to act oncogenically to stimulate the growth and spread of cancer cells. In particular, EGFR variants have been used as biomarkers for diagnosis and prognosis of brain cancer. The first identified and most common EGFR variant is EGFRvIII, which is an in-frame deletion corresponding to exons 2-7 in the mRNA. Other EGFR variants known in the art include: EGFRvI (N-terminal truncation), EGFRvII (deletion of exons 14-15), EGFRvIII (deletion of exons 2-7), EGFRvIII/Δ12-13 (deletion of exons 2-7 and exons 12-13), EGFRvIV (deletion of exons 25-27), EGFRvV (C-terminal truncation, EGFR.TDM/2-7 (tandem duplications of exons 2-7), EGFR.TDM/18-25 (tandem duplications of exons 18-25) and EGFR.TDM/18-26 (tandem duplications of exons 18-26).

Examples of biomarkers known in the art associated with neurodegenerative diseases include: APP (alpha and beta), Aβ42 (amyloid beta protein fragment), BACE-1, PSEN1, PSEN2, tau, and phosphorylated tau (PTAU). Combinations thereof may be used to detect a neurodegenerative disease.

The methods described herein may be particularly useful for diagnosing, prognosing, or monitoring neurological diseases or medical conditions, such as brain cancer and neurodegenerative diseases. Brain cancers include, for example, gliomas, astrocytic tumors (e.g., pilocytic astrocytoma, low-grade astrocytoma, and anaplastic astrocytoma), oligodendroglial tumors, gliobastomas, glioblastoma multiform (GBM), meningiomas, schwannomas, neuromas, ependymomas, craniopharyngiomas, pituitary tumors, pituitary adenoma, primary CNS lymphoma, primary lymphoma of the brain, pineal gland tumors, primary germ cell tumors of the brain, and metastatic brain cancers wherein the primary tumor originated from a tissue other than brain. Neurodegenerative diseases include those diseases characterized by loss or dysfunction of neurons or neuronal function in motor, sensory or cognitive systems, e.g., dementia, Alzheimer's disease, Parkinson's disease and Parkinsonian disorders, Pick's disease, Lewy body dementia, corticobasal degeneration, progressive supranuclear palsy, Huntington's disease, ataxia, multiple system atrophy, amyotrophic lateral sclerosis, spinal muscular atrophy, frontotemporal dementia, and prion diseases. Other brain diseases or medical conditions include, for example, traumatic brain injury, encephalitis, meningitis, or other infection of the brain, e.g., viral, bacterial or prion. Prion diseases include, for example, Creutzfeldt-Jakob Disease (CJD), Variant Creutzfeldt-Jakob Disease (vCJD), Gerstmann-Straussler-Schneinker Syndrome (GSS), fatal Familial Insomnia (FI), Kuru, transmissible spongiform encephalopathy (TSE) (e.g., bovine spongiform encephalopathy), chronic wasting disease (CWD) and scrapie. Familial forms of prion diseases are caused by inherited mutations in the PRNP gene. Prion proteins (PrP), and mutations thereof, can be detected by various protein-detecting methods known in the art, such as immunoprecipitation, western blot, ELISA and mass spectrometry approaches. Prion proteins can often be found in microvesicles or exosomes shed from diseased cells and can be readily isolated from cerebrospinal fluid using the methods described herein.

Many biomarkers have also been found to influence therapy selection for a particular patient. The detection of the presence or absence of such biomarkers in a nucleic acid extraction from isolated microvesicles, according to the methods disclosed herein, may aid in therapy selection in a given patient.

Selection of an individual from whom the particles are isolated is performed by the skilled practitioner based upon analysis of one or more of a variety of factors. Such factors for consideration are whether the subject has a family history of a specific disease (e.g., a cancer or a neurodegenerative disease), has a genetic predisposition for such a disease, has an increased risk for such a disease, has physical symptoms which indicate a predisposition, or environmental reasons. Environmental reasons include lifestyle, exposure to agents which cause or contribute to the disease such as in the air, land, water or diet. Other reasons to select an individual for performing the methods disclosed herein include previous history with the disease, being currently diagnosed with the disease prior to therapy or after therapy, being currently treated for the disease (undergoing therapy), or being in remission or recovery from the disease.

The methods described herein may also be useful for identifying novel biomarkers associated with diseases or medical conditions, such as a neurological disease or medical condition. The present invention provides methods for determining the gene expression profiles of a subject suffering from a disease or medical condition, and comparing the gene expression profile to a control profile of a subject that does not suffer from the disease or medical condition, thereby identifying the differentially expressed genes or sequences that can be novel biomarkers.

Kit

The present invention also provides a kit for use in the methods disclosed herein. The kit comprises: RNase or DNase inhibitor in quantity sufficient to mitigate adverse factors that prevent or might prevent nucleic acid extraction, RNA purification reagent; optionally, lysis buffer; and optionally, instructions for using the foregoing reagents in the extraction of nucleic acids from isolated particles. The RNA purification reagent helps to purify the released nucleic acids. The lysis buffer helps to break open microvesicles so that their nucleic acid contents are released. The use of DNASE or RNase inhibitor enhances the quality and quantity of the extracted nucleic acids. In some embodiments, DNase may be included in the nucleic acid extraction to enhance the quality of nucleic acid extraction, wherein the nucleic acid is RNA.

In some instances, the kit may further comprise instructions for using the kit. Instructions for using the kit may be put in the package with the other kit components or in a location accessible to the kit use (e.g., on a website or webpage accessible to the kit use). The content of the instructions may include, but is not limited to, instructions for how to perform the particle isolation, how to extract the nucleic acids, how to reconstitute reagents, how to use the lysis buffer, and how to carry out the whole procedure of obtaining nucleic acids by using the kit.

It should be understood that this invention is not limited to the particular methodologies, protocols and reagents described herein, which may vary. The terminology used herein is for the purpose of describing particular embodiments only, and is not intended to limit the scope of the present invention, which is defined solely by the claims.

Examples of the disclosed subject matter are set forth below. Other features, objects, and advantages of the disclosed subject matter will be apparent from the detailed description, figures, examples and claims. Methods and materials substantially similar or equivalent to those described herein can be used in the practice or testing of the presently disclosed subject matter. Exemplary methods and materials are now described as follows.

EXAMPLE 1

Particle Isolation and Nucleic Acid Extraction from Cerebrospinal Fluid Samples

From a university clinical research center, we obtained brain tissue biopsy samples and matched cerebrospinal fluid samples from glioblastoma patients. The glioblastoma in each set of samples was defined as stage 4 clinical astrocytoma. We designated two of the patients as Patient #1 and Patient #2.

For RNA extraction from brain biopsy tissues, the tissue cells were incubated in pre-chilled (−20° C.) RNAlater® storage reagent (Ambion) for at least 16 hours at −20° C. The biopsy was homogenized with a motorized disposable pestle and resuspended in Qiazol lysis buffer (Qiagen), then further processed to extract RNA using the miRNeasy RNA extraction protocol. The RNA was eluted in a final volume of 14 µl RNase-free water.

For RNA extraction from cerebrospinal fluids, the cerebrospinal fluid samples were filtered through a 0.8 µm filter (Millipore) and the filtrate was then stored at −80° C. for 24 hours. During the thaw process, 8 µl RNaseIn ribonuclease inhibitor (40 u/µl, Promega) was added into the sample. The sample was then ultracentrifuged at 120,000 g for 80 minutes and the pellet was used for nucleic acid extraction employing a modified miRNeasy RNA extraction protocol.

In this modified protocol, we treated the pellet at room temperature for 20 minutes with 8 µL RNaseIn mixture in 42 µL, PBS. RNaseIn was at a concentration of 40 units/µL.

Per sample:

| | |
|---|---|
| RNaseIn | 8 µL |
| 1xPBS | 42 µL |
| | 50 µL |

Then 700 µl Qiazol lysis buffer (Qiagen) was added to each sample in the centrifuge tube and mixed by pipetting up and down 15 times to dissolve/resuspend the pellet. The suspended pellet mixture was immediately transferred to an Eppendorf tube. Further nucleic acid extraction was then performed in a PCR hood. The tube with the pellet mixture was vortexed briefly and incubated at room temperature for 2-4 minutes before 90 µl chloroform was added into the tube containing the mixture. The tube was then capped, shaken vigorously for 20 seconds, incubated at room temperature for 2-3 minutes, and centrifuged for 15 minutes at 12,000 g at 4° C. The upper aqueous phase was transferred to a new collection tube into which, 1.5 volumes (usually 600 µl) of 100% ethanol was added and mixed thoroughly by pipetting up and down several times.

Up to 700 µl of the ethanol mixture, including any precipitate that may have formed, was transferred into an RNeasy Micro spin column (MinElute column stored @ +4° C., the column comes with the RNeasy Micro kit and not the MIRNEASY kit) which was inserted in a 2 ml collection tube as supplied by the manufacturer, and centrifuged at 1000 g for 15 seconds at room temperature. The flow-through was discarded. The centrifugation step was repeated until all the remaining mixture had been added. Again, the flow-through was discarded. The nucleic acids on the column were then washed three times as follows: 1) 700 µL Buffer RWT was added onto the RNeasy MinElute spin column and centrifuged for 15 seconds at 8500 g to wash the column with the flow-through discarded; 2) 500 µL Buffer RPE was added onto the RNeasy MinElute spin column and centrifuged for 15 seconds at 8500 g to wash the column with the flow-through discarded; 3) repeat the Buffer RPE wash step except that the column was centrifuged for 2 minutes at 8500 g to dry the RNeasy Mini spin column membrane.

After the washing steps, the RNeasyMinElute spin column was inserted into a new 2 ml collection tube and centrifuged at 14000 g for 5 minutes to further dry the column membrane. The dried column was inserted into another new 1.5 ml collection tube and 16 µL, RNase-free water was added onto the dried column membrane and incubated for 1 minute at room temperature. The nucleic acids were eluted by centrifugation for 1 minute at 8500 g. The volume of the eluted nucleic acids was about 14 µl.

We measured the expression of GAPDH, 18S RNA, and EGFRvIII genes in the extracted nucleic acids using RT-PCR analysis. We used 12 µl of the extracted RNA and reverse transcribed the RNA into cDNA using Sensiscript kit (Qiagen) according to the manufacturer's protocol with slight modifications. In this modified protocol, the primers used for reverse transcription may be random primers, gene specific primers, oligo-dT primers, or a mixture of any of the three types of primers. Briefly, we prepared master mix on ice according to Table 1. Here we used a mixture of random nonamers and oligo-dT primers in the master mix. The master mix contained all components required for first-strand synthesis except the template RNA. We mixed an aliquot of the master mix with template RNA and incubated the reaction for 80 minutes at 37° C.

TABLE 1

| RT-PCR reaction components | | |
|---|---|---|
| Component | Volume/reaction | Final concentration |
| Master Mix | | |
| 10x buffer RT | 2 µl | 1x |
| dNTP mix (5 mM each dNTP) | 2 µl | 0.5 mM each dNTP |
| Oligo-dT primer (50 µM) | 0.4 µl | 1 uM |
| Random nonamers (50 µM) | 2 µl | |
| SuperaseIn (20 U/µl) (RNase inhibitor) | 0.5 µl | 10 units/reaction |
| Sensiscript Reverse Transcriptase | 1 µl | — |
| RNase free water | Variable (—) | — |
| Template RNA | | |
| Template RNA, add last | Variable(12.1 µl) | Max 50 ng/reaction |
| Total volume | 20 µl | |

We then used 1 µl of the resulting cDNA product as templates to perform Real-time PCR. The primers used for RT-PCR were commercially obtained from Applied Biosystems, as follows: Human GAPDH (part number 4326317E); 18S rRNA (part number Hs99999901_s1). We specially designed the primers used for detecting the EGFRvIII gene variant. As shown in Table 2, the primers for detecting the EGFRvIII gene variant are as follows: EGFR Forward 1: CTGCTGGCTGCGCTCTG (SEQ ID NO:1); EGFRvIII Reverse 4 (spanning junction): CGTGATCTGTCACCA-CATAATTACC (SEQ ID NO:2); EGFR probe 6 (FAM labeled MGB probe anti-sense strand): TTCCTCCAGAGC-CCGACT (SEQ ID NO:3).

TABLE 2

| Primer sequences for EGFRvIII gene | | |
|---|---|---|
| SEQ ID | Primer name | Sequence |
| 1 | EGFR Forward 1 | CTGCTGGCTGCGCTCTG |
| 2 | EGFRv3 Reverse 4 | CGTGATCTGTCACCACATAATTACC |
| 3 | EGFR probe 6 (FAM labeled MGB probe anti-sense strand) | TTCCTCCAGAGCCCGACT |

Figure 1B:
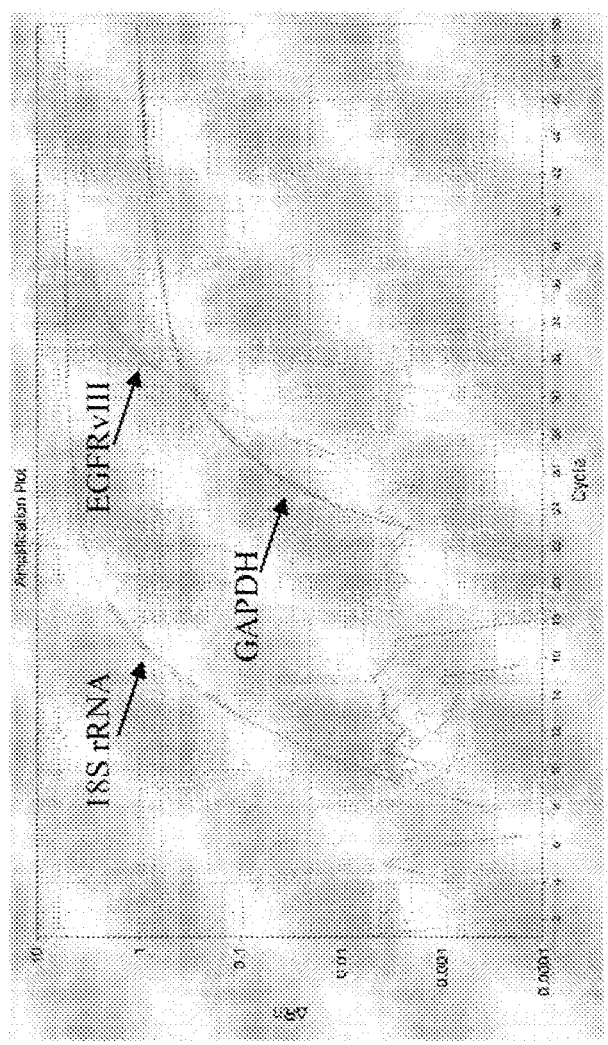
Figure 2A:
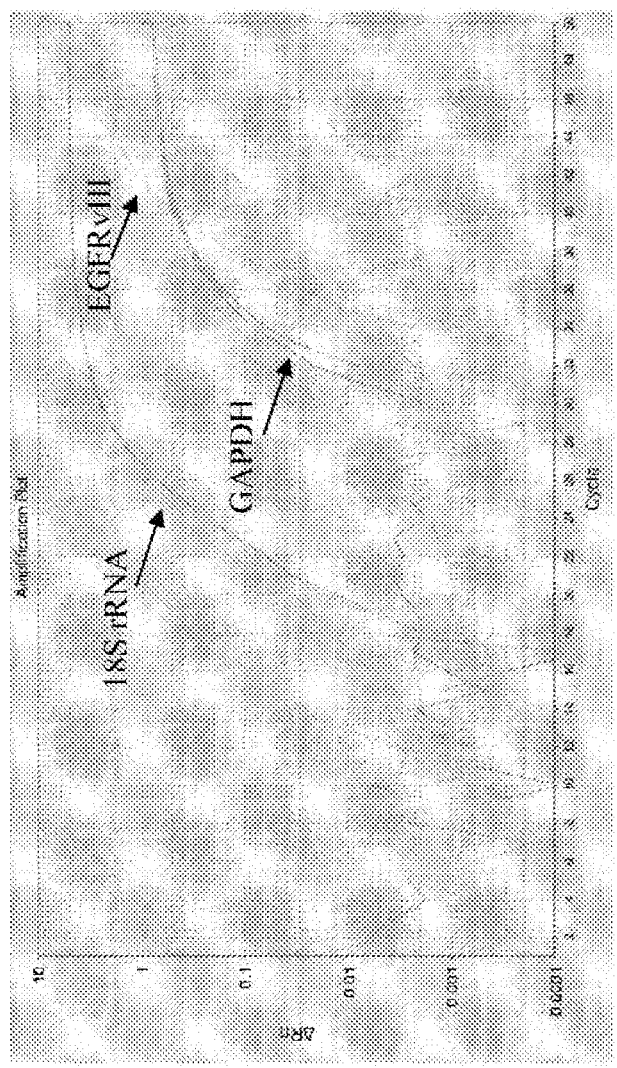
FIGS. 2A and 2B are plots showing similar EGFRvIII amplification curves to those in FIGS. 1A and 1B, except that the matched brain biopsy tissue (FIG. 2A) and cerebrospinal fluid (FIG. 2B) samples were from a different glioblastoma patient (Patient #2).
Figure 2B:
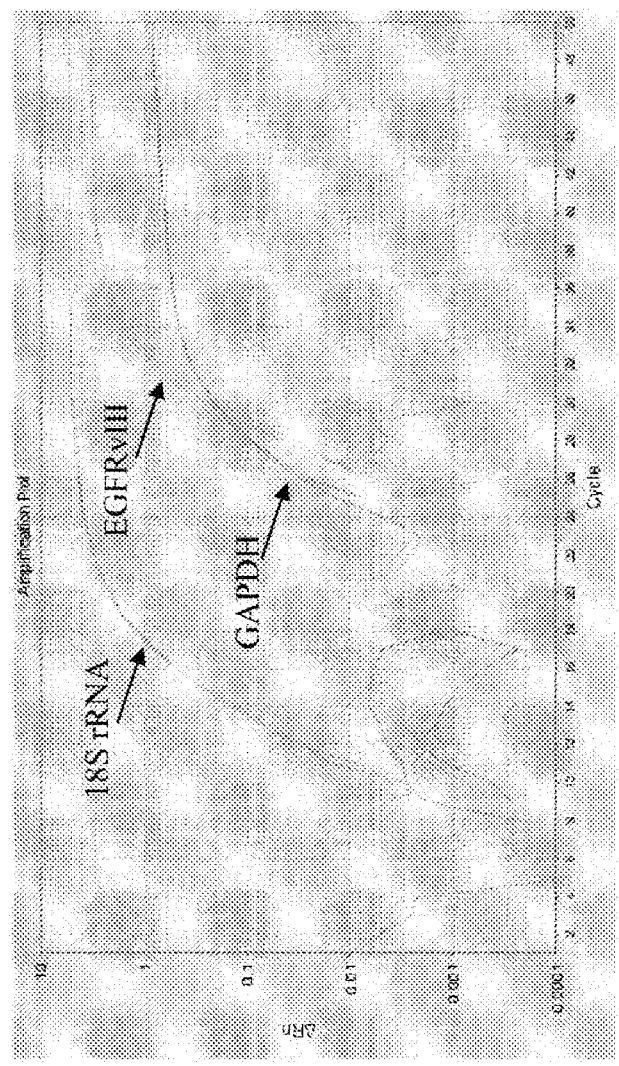
Figure 3:
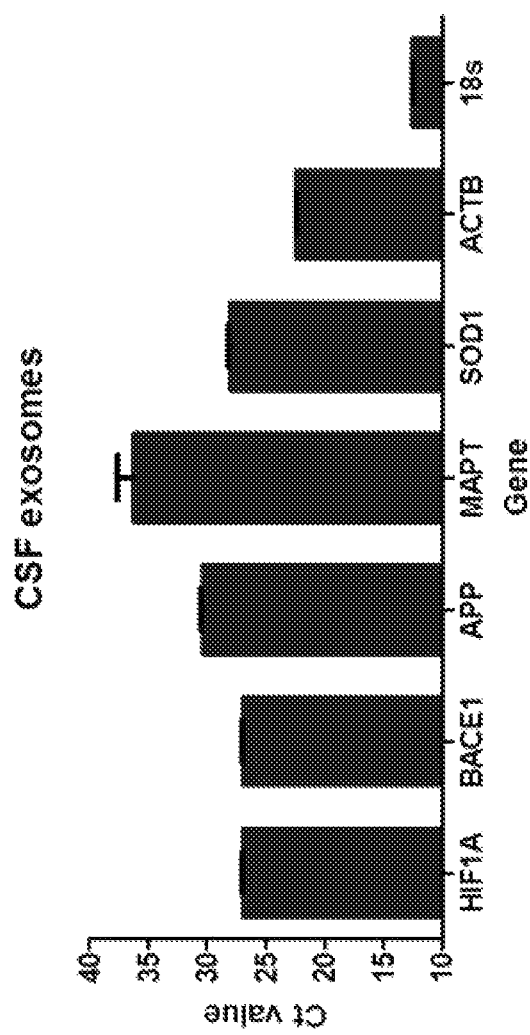
FIG. 3 is a graph showing qRT-PCR analysis and average values of the indicated brain-associated genes. The y-axis indicates the cycle threshold±standard error of the mean.

As shown in FIG. 1A, the expression of EGFRvIII, GAPDH, and 18S rRNA can be detected in the RNA extraction from the brain biopsy tissue cells from Patient #1. Similarly, as shown in FIG. 1B, the expression of EGFRvIII, GAPDH, and 18S rRNA can be detected in the RNA extraction from the cerebrospinal fluid sample from the same Patient #1. As shown in FIGS. 2A (biopsy sample) and 2B (cerebrospinal fluid sample), the expression of EGFRvIII, GAPDH, and 18S rRNA were observed in RNA extracted from the samples from Patient #2. Therefore, using the new method as disclosed in this invention, we were able to isolate nucleic acid-containing particles from cerebrospinal fluid samples. The nucleic acids extracted from the isolated particles contained RNAs for at least EGFRvIII, GAPDH, and 18S rRNA genes, suggesting that the extracted nucleic acids from serum particles may include RNAs corresponding to many other genes.

EXAMPLE 2

Detection of Brain-Associated Gene Expression in CSF Samples

Our data shows that RNA transcriptome analysis can be performed on nucleic acid-containing particles isolated from CSF samples and the analysis can subsequently be used to aid in the diagnosis, prognosis or monitoring of a disease or evaluation of treatment efficacy of a subject undergoing treatment. We have shown that abundant RNA can be isolated in a reproducible manner from CSF particles, such as exosomes or particles, even after storage at −80° C. for several years, such as in biobanks.

Here, we show that brain-associated gene expression can be easily detected from RNA isolated from CSF samples. To obtain a baseline and the average gene expression level in normal CSF particles, we pooled CSF from 36 individuals and performed 3 replicate exosome purifications. Specifically, RNA was extracted 3 times from the same CSF batch, at a volume of 4 ml each. This also gave us a measure of the assay reproducibility (exosome isolation and qRT-PCR) evaluated as the mean±standard error of the mean (SEM). CSF particles were isolated using the methods described herein, such as the method described in Example 1. RNA was extracted and synthesized to cDNA. Gene expression was determined by using quantitative real-time PCR (qRT-PCR). The genes examined were brain related genes often dysregulated in neurodegenerative disorders, including PD, as well as house-keeping genes commonly used as a control. The genes examined were: HIF1A (hypoxia-inducible factor 1), BACE1 (beta-site amyloid precursor protein cleaving enzyme 1), APP (amyloid precursor protein), MAPT (also known as Tau or microtubule associated protein), SOD1 (superoxide dismutase 1), ACTB (beta-actin) and 18S rRNA (18S ribosomal RNA). The qRT-PCR values are displayed as the average cycle threshold±standard error of the mean.

All 7 genes were reproducibly detected, indicating good feasibility of gene expression profiling in particles isolated from the CSF. Furthermore, this example shows that neurodegenerative disease-specific genes, or biomarkers, can be specifically assessed in a patient and compared to reference samples or controls to aid in the diagnosis, prognosis or monitoring of a disease or for evaluation of treatment efficacy of a particular therapeutic regimen.

EXAMPLE 3

Gene Expression Analysis of CSF Samples from Alzheimer's Patients

In this example, we show gene expression analysis of Alzheimer's patients compared to age and gender-matched control subjects. RNA extracted from CSF particles, such as exosomes and particles, can be analyzed for specific biomarkers. Here we show that nucleic acids extracted from CSF particles can be used to find differential gene expression patterns in Alzheimer's patients compared to controls. Thus, the methods of the present invention can be used to identify new biomarkers useful for the diagnosis, prognosis, monitoring of a disease or medical condition, or determining therapeutic efficacy of a certain therapeutic regimen.

Samples were collected from Alzheimer's patients and age-matched control patients with subjective memory complaints (SMC). The patient cohort is summarized in Table 3.

TABLE 3

Summary of patient cohort (10 Alzheimer's patients, 10 SMC patients)

| Code | Age | Sex | Diag | L_AB42 | L_TAU | L_PTAU | fup_diag | V_MMSE |
|---|---|---|---|---|---|---|---|---|
| 128 | 71.4 | m | AD | 446 | 869 | 102 | #NULL! | 27 |
| 236 | 60.9 | f | AD | 345 | 1,946 | 184 | #NULL! | 16 |
| 308 | 71.9 | m | AD | 457 | 1,536 | 132 | #NULL! | 7 |
| 310 | 67.7 | m | AD | 487 | 491 | 73 | #NULL! | 19 |
| 328 | 69.5 | m | AD | 292 | 470 | 73 | #NULL! | 10 |
| 337 | 59.9 | m | AD | 228 | 387 | 54 | #NULL! | 25 |
| 358 | 61.8 | f | AD | 502 | 928 | 113 | #NULL! | 18 |
| 375 | 68.1 | f | AD | 398 | 1,356 | 139 | #NULL! | 12 |
| 390 | 55.3 | f | AD | 726 | 2,272 | 152 | #NULL! | 23 |
| 394 | 54.4 | f | AD | 349 | 288 | 32 | #NULL! | 24 |
| 409 | 55.1 | f | SMC | 805 | 288 | 35 | 2.1 | 30 |
| 414 | 76.8 | m | SMC | 549 | 154 | 22 | 2.3 | 29 |
| 415 | 50.3 | f | SMC | 818 | 189 | 33 | 2.3 | 30 |
| 464 | 78.0 | f | SMC | 638 | 284 | 44 | #NULL! | 29 |
| 480 | 55.3 | m | SMC | 989 | 283 | 41 | #NULL! | 27 |
| 486 | 71.5 | f | SMC | 605 | 274 | 38 | 5.0 | 30 |
| 504 | 45.1 | m | SMC | 939 | 290 | 41 | 5.7 | 30 |
| 526 | 72.1 | m | SMC | 844 | 320 | 46 | 4.0 | 30 |
| 543 | 51.2 | m | SMC | 974 | 247 | 36 | 1.0 | 28 |
| 546 | 66.3 | m | SMC | 695 | 212 | 38 | 5.2 | 28 |

MMSE = Mini Mental State Exam
Maximum MMSE score = 30 points
20 to 24 suggests mild dementia
13 to 20 suggests moderate dementia
<12 indicates severe dementia
On average, the MMSE score of a person with Alzheimer's declines about 2-4 points each year.
L_AB42, L_TAU, L_PTAU values represent the clinical measurements of the protein levels of amyloid-beta 42, Tau and phosphorylated Tau (PTAU).

2 ml of CSF sample were collected from 10 Alzheimer's patients and 10 SMC patients. The samples were blinded. CSF particle purification and RNA extraction was performed using the methods described herein.

Specifically, the extracted RNA was reverse transcribed, pre-amplified and analyzed according to the recommended protocol from Applied Biosystems/Life Technologies for the TaqMan OpenArray microRNA Panel (Publication Part Number 4461306 Rev B). Briefly, the RNA was reverse transcribed with the Megaplex RT reactions (Pool A and Pool B), pre-amplified, diluted and analyzed on the OpenArray.

The extracted RNA was subjected to miRNA profiling by using the ABI Open Array platform, which contains 758 miRNAs and controls. Roughly 100 miRNAs were detected in each sample. U6 was used as a control gene for normalization. Our results indicate that there is a general downregulation of miRNA in AD patients compared to control patients. This is consistent with the findings of Schonrock et al., which showed a similar downregulation of miRNAs in neurons after exposure to the amyloid beta peptide, Aβ42.

Figure 4:
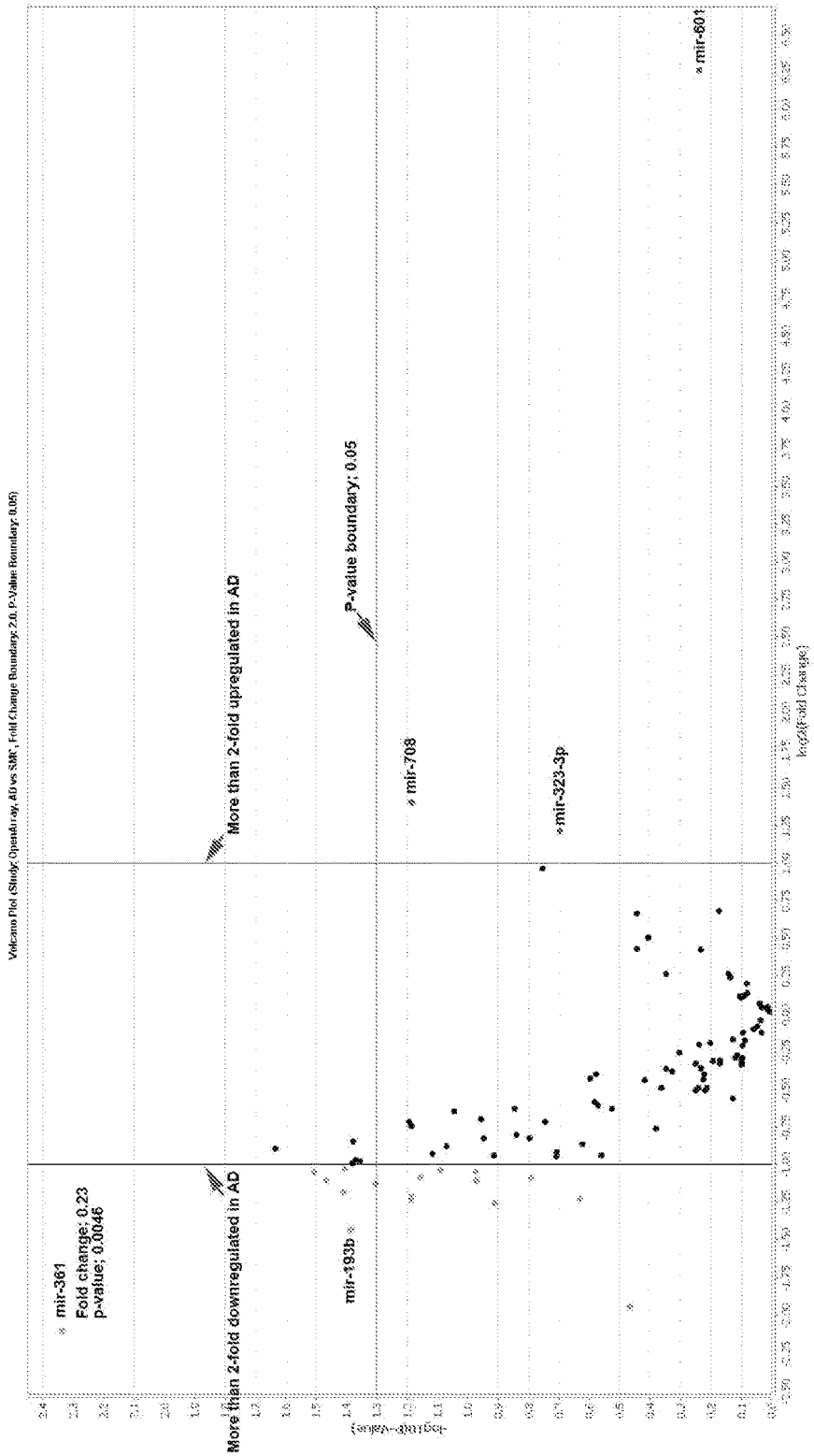
FIG. 4 is a volcano plot comparing the CSF microvesicle miRNA profile of Alzheimer's disease patients to age-matched patients with subjective memory complaints without Alzheimer's disease. The miRNA levels from each patient were normalized to U6 RNA. Each dot represents a miRNA, where the differential expression of the miRNA compared to the controls is shown on the x-axis and the p-value shown on the y-axis.
Figure 5:
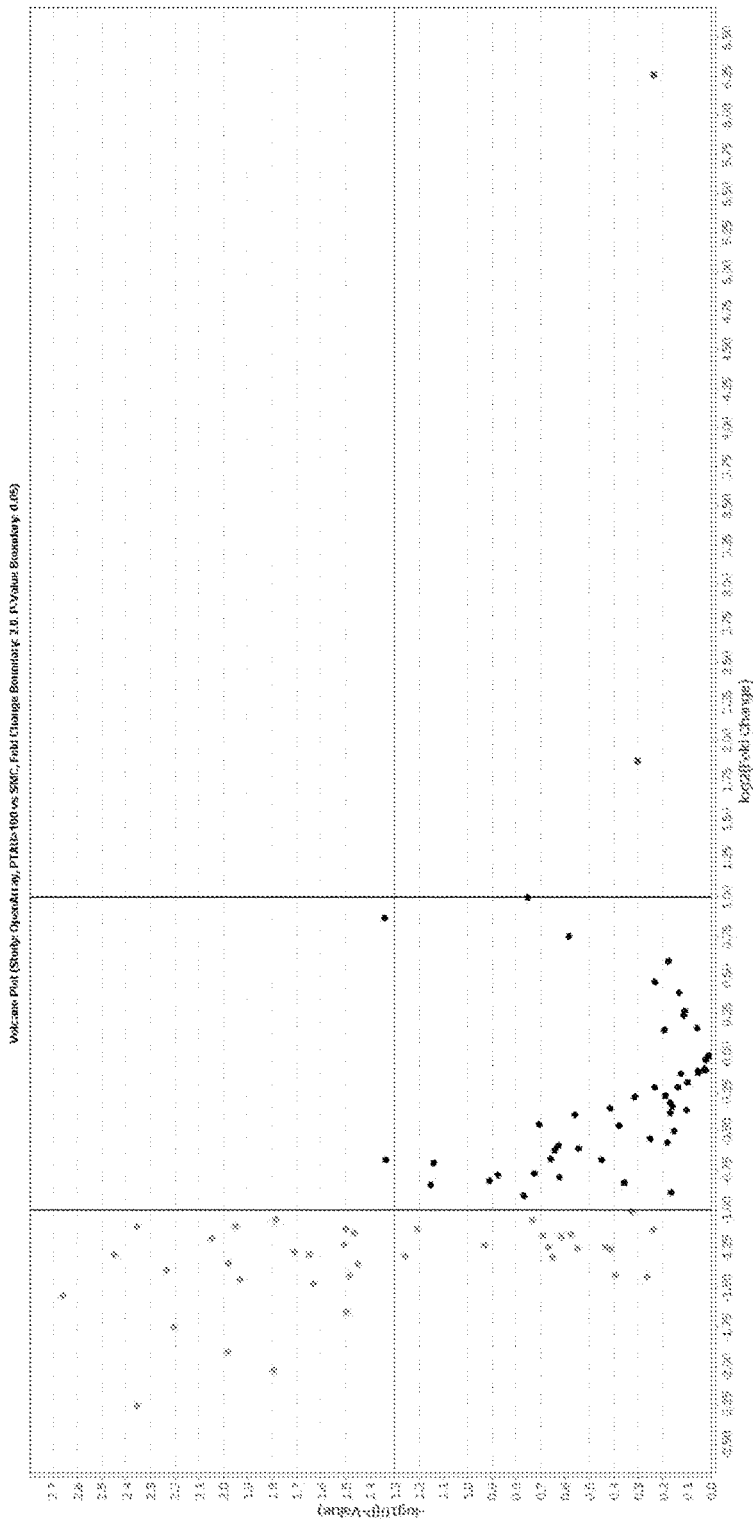
FIG. 5 is a volcano plot comparing the CSF microvesicle miRNA profile of Alzheimers disease patients with a PTAU protein level above 100 to age-matched patients with subjective memory complaints, and without Alzheimer's disease. The miRNA levels from each patient were normalized to U6 RNA. Each dot represents a miRNA, where the differential expression of the miRNA compared to the controls is shown on the x-axis and the p-value shown on the y-axis.
Figure 6:
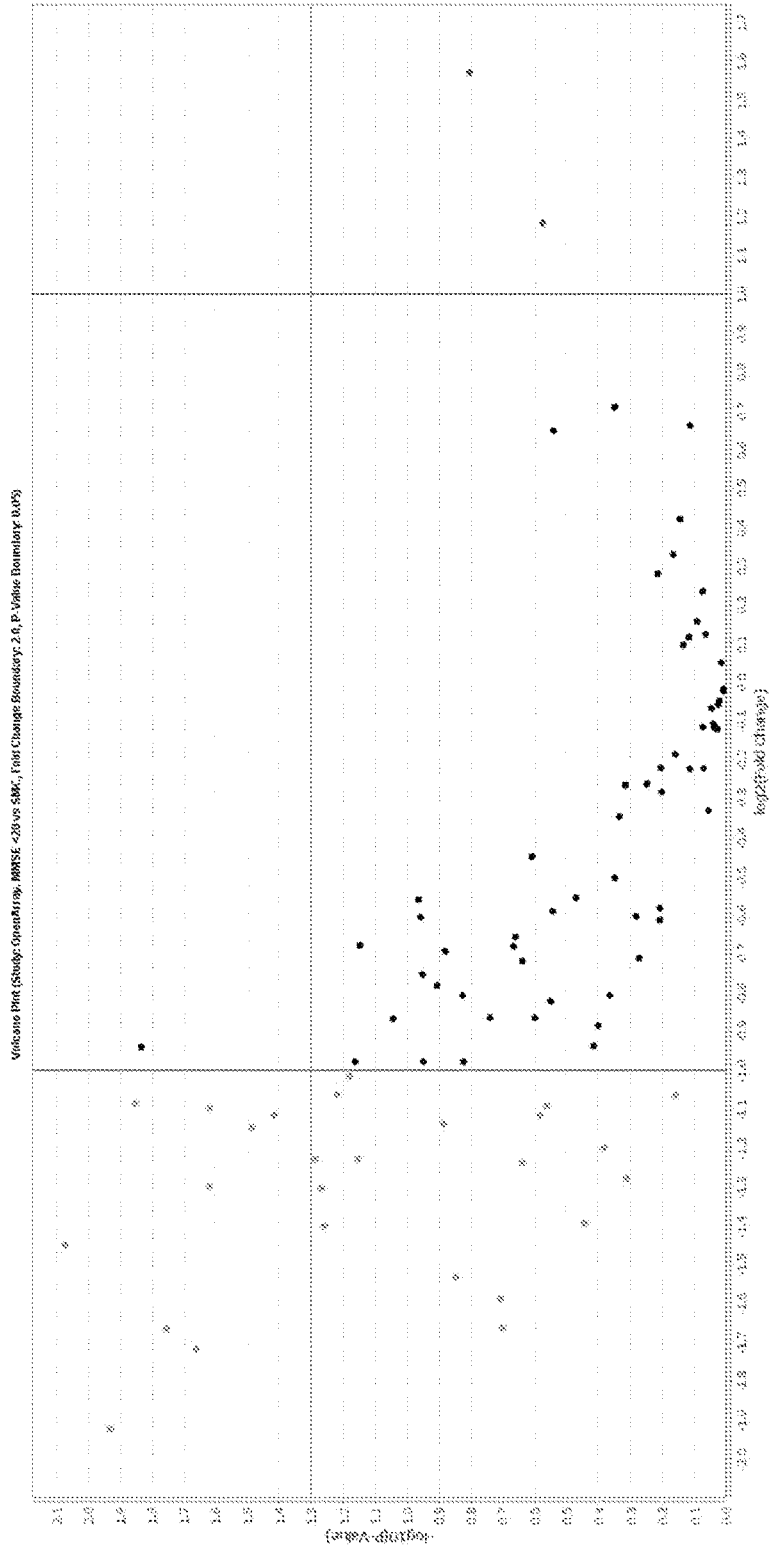
FIG. 6 is a volcano plot comparing the CSF microvesicle miRNA profile of Alzheimer's disease patients with a minimental state exam (MMSE) score below 20 to age-matched patients with subjective memory complaints, and without Alzheimer's disease. The miRNA levels from each patient were normalized to U6 RNA. Each dot represents a miRNA, where the differential expression of the miRNA compared to the controls is shown on the x-axis and the p-value shown on the y-axis.

After the miRNA levels from each patient were normalized to U6 RNA, the data was plotted in a series of volcano plots, as depicted in FIGS. 4, 5 and 6. For each volcano plot, each dot represents a miRNA, where the differential expression of the miRNA compared to the controls is shown on the x-axis and the p-value shown on the y-axis. For example, FIG. 4 shows that the CSF microvesicle miRNA profile of Alzheimer's disease patients is different from age-matched patients with subjective memory complaints without Alzheimer's disease. Similarly, FIG. 5 demonstrates that the CSF microvesicle miRNA profile of Alzheimers disease patients with a PTAU (phosphorylated tau) protein level above 100 is different from age-matched patients with subjective memory complaints, and without Alzheimer's disease. FIG. 6 shows that the CSF microvesicle miRNA profile of Alzheimer's disease patients with a mini-mental state exam (MMSE) score below 20 is different from age-matched patients with subjective memory complaints, and without Alzheimer's disease.

Several miRNAs of particular interest were identified. miR-361 was found significantly downregulated in the AD tissue and also in the CSF particles in the present patient cohort dataset. miR-302c is very abundant in 5 AD samples and 1 SMC sample, but not detected in the remaining 14 samples. miR-324-5p was detected in 7 SMC samples, but not detected in any AD samples. Detection of differential miRNA expression in AD patients compared to SMC demonstrates the utility of the present invention for identifying biomarkers, such as miRNAs, that may be useful for diagnosis, prognosis, or monitoring a disease or medical condition, such as Alzheimer's disease. The miRNAs described in this example are intended to highlight the feasibility of identification of biomarker miRNAS and are not meant to limit the scope of the invention to the described miRNAs.

REFERENCES

Chen, C., J. Skog, C. H. Hsu, R. T. Lessard, L. Balaj, T. Wurdinger, B. S. Carter, X. O. Breakefield, M. Toner, and D. Irimia. 2010. Microfluidic isolation and transcriptome analysis of serum microvesicles. *Lab Chip.* 10:505-11.

Cheruvanky, A., H. Zhou, T. Pisitkun, J. B. Kopp, M. A. Knepper, P. S. Yuen, and R. A. Star. 2007. Rapid isolation of urinary exosomal biomarkers using a nanomembrane ultrafiltration concentrator. *Am J Physiol Renal Physiol.* 292:F1657-61.

Miranda, K. C., D. T. Bond, M. McKee, J. Skog, T. G. Paunescu, N. Da Silva, D. Brown, L. M. Russo. 2010. Nucleic acids within urinary exosomes/microvesicles are potential biomarkers for renal disease. *Kidney Int.* 78(2): 191-9.

Nilsson, J., J. Skog, A. Nordstrand, V. Baranov, L. Mincheva-Nilsson, X. O. Breakefield, and A. Widmark. 2009. Prostate cancer-derived urine exosomes: a novel approach to biomarkers for prostate cancer. *Br J Cancer.* 100:1603-7.

Raposo, G., H. W. Nijman, W. Stoorvogel, R. Liejendekker, C. V. Harding, C. J. Melief, and H. J. Geuze. 1996. B lymphocytes secrete antigen-presenting vesicles. *J Exp Med.* 183:1161-72.

Skog, J., T. Wurdinger, S. van Rijn, D. H. Meijer, L. Gainche, M. Sena-Esteves, W. T. Curry, Jr., B. S. Carter, A. M. Krichevsky, and X. O. Breakefield. 2008. Glioblastoma microvesicles transport RNA and proteins that promote tumour growth and provide diagnostic biomarkers. *Nat Cell Biol.* 10:1470-6.

Taylor, D. D., and C. Gercel-Taylor. 2008. MicroRNA signatures of tumor-derived exosomes as diagnostic biomarkers of ovarian cancer. *Gynecol Oncol.* 110:13-21.

What is claimed is:

1. A method for diagnosis, prognosis, monitoring or therapy selection for a disease or medical condition of a subject, comprising the steps of:
   a. obtaining a cerebrospinal fluid (CSF) sample from a subject;
   b. processing the CSF sample to remove cells and cell debris and isolating microvesicles from the CSF sample, wherein the processing comprises
      (i) pre-processing comprising one or more centrifugation steps at a speed in the range of 100-500 g, at a speed in the range of 2,000-200,000 g, or a combination thereof, one or more filtration steps using a filter having a size in the range of 0.1-1.0 μm, or a combination thereof
      (ii) followed by isolating the microvesicles from the sample, wherein isolating comprises one or more centrifugation steps, size exclusion chromatography, density gradient centrifugation, differential centrifugation, nanomembrane ultrafiltration, filtration concentration, immunoabsorbent capture, affinity purification, ion exchange chromatography, microfluidic separation, or combinations thereof;
   c. extracting one or more nucleic acids from the microvesicles;
   d. detecting a level of expression for a biomarker associated with a disease or medical condition in the extracted nucleic acids, and detecting a level of expression of a reference gene in the extracted nucleic acids, wherein the reference gene is a brain-associated gene; and
   e. determining a normalized, relative expression level of the biomarker, wherein the relative expression level of the biomarker is a ratio between the level of biomarker expression to the level of reference gene expression,
   wherein the subject is identified as suffering from, or being at an increased risk for, the disease or medical condition when the relative expression level of the biomarker is greater than or less than a cutoff level of biomarker expression, wherein the cutoff level of biomarker expression is a score based on a collective level of biomarker expression in a control group of subjects that are not suffering from the medical condition of the brain or wherein the cutoff level of biomarker expression is a score based on a collective level of biomarker expression in a control group of subjects that have been diagnosed with a low level or early stage of the disease or medical condition.

2. The method of claim 1, wherein the reference gene is U6.

3. The method of claim 1, wherein the biomarker is:
   a. a species of nucleic acid;
   b. the level of expression of a nucleic acid;
   c. a nucleic acid variant; or
   d. a combination thereof.

4. The method of claim 1, wherein the biomarker is messenger RNA, microRNA, siRNA or shRNA.

5. The method of claim 1, wherein the biomarker is associated with the brain.

6. The method of claim 1, wherein the biomarker is associated with glioblastoma or other brain cancer.

7. The method of claim 1, wherein the biomarker is a nucleic acid corresponding to an EGFR variant.

8. The method of claim 7, wherein the EGFR variant is EGFRvIII.

9. The method of claim 1, wherein the biomarker is associated with Alzheimer's disease or other neurodegenerative disease.

10. The method of claim 1, wherein the biomarker is a nucleic acid corresponding to APP, Aβ42, BACE-1, Tau or a combination thereof.

11. The method of claim 1, wherein the subject or patient is a human subject or patient.

12. The method of claim 11, wherein the subject or patient is a pediatric subject or patient.

13. The method of claim 1, wherein disease or other medical condition is a brain cancer or a neurodegenerative disease.

14. The method of claim 13, wherein the brain cancer is glioblastoma.

15. The method of claim 13, wherein the neurodegenerative disease is Alzheimer's disease.

16. The method of claim 1, wherein the biomarker is a nucleic acid and the method further comprises amplification of the nucleic acid.

17. The method of claim 1, wherein the detecting in step d) is performed by microarray analysis, PCR, hybridization with allele-specific probes, enzymatic mutation detection, ligation chain reaction (LCR), oligonucleotide ligation assay (OLA), flow-cytometric heteroduplex analysis, chemical cleavage of mismatches, mass spectrometry, nucleic acid sequencing, single strange conformation polymorphism (SSCP), denaturing gradient gel electrophoresis (DGGE), temperature gradient gel electrophoresis (TGGE), restriction fragment polymorphisms, serial analysis of gene expression (SAGE) or combinations thereof.

18. The method of claim 1, wherein the CSF sample is subjected to storage in a 4° C. environment prior to processing.

19. The method of claim 1, wherein the CSF sample is subjected to storage in a less than −70° C. environment prior to processing.

20. A method for diagnosis, prognosis, monitoring or therapy selection for a disease or medical condition of a subject, comprising the steps of:
   a. obtaining a cerebrospinal fluid (CSF) sample from a subject;
   b. processing the CSF sample to remove cells and cell debris and isolating microvesicles from the CSF sample, wherein the processing comprises (i) pre-processing comprising one or more centrifugation steps at a speed in the range of 100-500 g, at a speed in the range of 2,000-200,000 g, or a combination thereof, one or more filtration steps using a filter having a size in the range of 0.1-1.0 µm, or a combination thereof (ii) followed by isolating the microvesicles from the sample, wherein isolating comprises one or more centrifugation steps, size exclusion chromatography, density gradient centrifugation, differential centrifugation, nanomembrane ultrafiltration, filtration concentration, immunoabsorbent capture, affinity purification, ion exchange chromatography, microfluidic separation, or combinations thereof;

c. extracting one or more nucleic acids from the microvesicles;

d. detecting a level of expression for a biomarker associated with a disease or medical condition in the extracted nucleic acids, and detecting a level of expression of a reference gene in the extracted nucleic acids, wherein the reference gene is a brain-associated gene; and e. determining a normalized, relative expression level of the biomarker, wherein the relative expression level of the biomarker is a ratio between the level of biomarker expression to the level of reference gene expression, wherein the subject is identified as suffering from, or being at an increased risk for, the disease or medical condition when the relative expression level of the biomarker is greater than or less than a cutoff level of biomarker expression or wherein the cutoff level of biomarker expression is a score based on a collective level of biomarker expression in a control group of subjects that have been diagnosed with a low level or early stage of the disease or medical condition.

* * * * *